United States Patent
Bittner et al.

(10) Patent No.: US 8,083,724 B2
(45) Date of Patent: Dec. 27, 2011

(54) PANTS-TYPE DISPOSABLE ABSORBENT HYGIENE ARTICLE

(75) Inventors: Manuela Bittner, Heidenheim (DE); Sascha Jovanov, Heidenheim (DE); Fridmann Hornung, Lauchheim (DE)

(73) Assignee: Paul Hartmann AG, Heidenheim (DE)

( * ) Notice: Subject to any disclaimer, the term of this patent is extended or adjusted under 35 U.S.C. 154(b) by 121 days.

(21) Appl. No.: 12/320,540

(22) Filed: Jan. 29, 2009

(65) Prior Publication Data
US 2009/0204094 A1 Aug. 13, 2009

Related U.S. Application Data

(63) Continuation of application No. 11/628,467, filed as application No. PCT/EP2005/006235 on Jun. 10, 2005, now abandoned.

(30) Foreign Application Priority Data

Jun. 29, 2004 (DE) .................. 10 2004 032 377

(51) Int. Cl.
*A61F 13/15* (2006.01)
(52) U.S. Cl. ........................... 604/385.24; 604/385.25
(58) Field of Classification Search ............. 604/385.24, 604/385.25
See application file for complete search history.

(56) References Cited

U.S. PATENT DOCUMENTS

| | | | |
|---|---|---|---|
| 4,323,070 A | 4/1982 | Ternstrom | |
| 4,895,568 A | 1/1990 | Enloe | |
| 5,622,581 A | 4/1997 | Ducker | |
| 5,735,839 A | 4/1998 | Kawaguchi | |
| 6,306,122 B1 | 10/2001 | Narawa | |
| 6,478,786 B1 * | 11/2002 | Glaug et al. | 604/385.27 |
| 6,520,945 B1 | 2/2003 | Hansson | |
| 6,554,815 B1 | 4/2003 | Umebayashi | |
| 6,569,139 B1 * | 5/2003 | Datta et al. | 604/385.27 |
| 6,743,321 B2 * | 6/2004 | Guralski et al. | 156/250 |
| 6,767,343 B2 * | 7/2004 | Shimada et al. | 604/385.25 |
| 7,094,227 B2 | 8/2006 | Ishiguro | |
| 7,449,014 B2 * | 11/2008 | Oba et al. | 604/385.25 |

(Continued)

FOREIGN PATENT DOCUMENTS

| | | |
|---|---|---|
| DE | 102 96 421 | 12/2003 |
| DE | 698 26 718 | 2/2005 |
| EP | 1 354 576 | 10/2003 |

(Continued)

*Primary Examiner* — Loan Thanh
*Assistant Examiner* — Lynne Anderson
(74) *Attorney, Agent, or Firm* — Paul Vincent

(57) ABSTRACT

A disposable article, comprises a chassis having a first waist region, a second waist region, and a crotch region extending in a longitudinal direction of said chassis between said first and said second waist regions. Transversely opposite side edges of said first and said second waist regions are bonded together to define a waist opening and two leg openings and a peripheral edge of each of said leg openings comprises a front portion and a rear portion, each of which has a first elasticized section which is located toward a respective front or rear waist region and along which said peripheral edge is elasticized about a respective said leg opening, a second non-elasticized section which is located toward said crotch region and along which said peripheral edge is not elasticized circumferentially about a respective said leg opening, and a third elasticized section which is located, in a longitudinal direction, between said second non-elasticized sections of said front and rear portions of each said leg opening and along which said crotch region is elasticized in a transverse direction of the article. The wearing comfort of the absorbent hygiene article is thereby improved and skin irritation is reduced.

6 Claims, 2 Drawing Sheets

U.S. PATENT DOCUMENTS

| | | |
|---|---|---|
| 2002/0072728 A1* | 6/2002 | Shinohara et al. ....... 604/385.29 |
| 2002/0165516 A1 | 11/2002 | Datta |
| 2003/0135189 A1 | 7/2003 | Umebayashi |
| 2004/0030317 A1 | 2/2004 | Torigoshi |
| 2004/0068246 A1 | 4/2004 | Rose |
| 2005/0055005 A1 | 3/2005 | Cazzato |

FOREIGN PATENT DOCUMENTS

| | | |
|---|---|---|
| EP | 1 384 459 | 1/2004 |
| WO | WO 00/02511 | 1/2000 |
| WO | WO 01/85082 | 11/2001 |
| WO | WO 2004/019838 | 3/2004 |

* cited by examiner

PANTS-TYPE DISPOSABLE ABSORBENT HYGIENE ARTICLE

The present application is a continuation of U.S. patent application Ser. No. 11/628,467, filed Dec. 4, 2006 now abandoned, which is based on International Application No. PCT/EP2005/006235, filed on Jun. 10, 2005, which in turn corresponds to German Application No. 10 2004 032 377.1, filed on Jun. 29, 2004, and priority is hereby claimed under 35 USC §119 based on these applications. These applications are hereby incorporated by reference in their entireties into the present application.

BACKGROUND OF THE INVENTION

The invention concerns a pants-type disposable absorbent hygiene article with a hip edge which is continuously closed in the peripheral direction and forms a hip opening, and with leg openings, wherein the hip edge which is continuously closed in the peripheral direction and the leg openings are formed by connecting longitudinal side edge sections of a front part and rear part to each other at the manufacturing plant, and having an absorbent body and elasticizing means at least in the area of the leg openings.

Conventional pants-type absorbent hygiene articles of this type usually comprise a plurality of elasticizing means, often in the form of rubber-elastic threads, which are mostly glued to chassis materials in the pretensioned state. A hip edge area is thereby usually preferably continuously elasticized in the peripheral direction. Conventional pants-type diapers also have elasticizing means in the front and rear areas. The peripheral areas forming or surrounding the leg openings are also continuously elasticized to ensure tight fit of the hygiene article on the skin surface of the user in order to prevent lateral escape of body excretions.

Abutment of pretensioned, elasticized areas on the skin surface especially in the area of the leg openings can cause skin irritations due to friction or force exerted by the mostly thread-shaped elasticizing means. This problem is aggravated by the presence of additional moisture within the hygiene article due to body liquids or perspiration and is aggravated by increasing activity, i.e. movement of the user.

Departing therefrom, it is the underlying purpose of the present invention to improve the wearing comfort of absorbent hygiene articles of the above-mentioned type and, in particular, reduce skin irritation.

SUMMARY OF THE INVENTION

This object is achieved in accordance with the invention with a hygiene article of this type in that a first elasticizing peripheral section, adjacent thereto, a second non-elasticizing peripheral section, adjacent thereto, a third elasticizing peripheral section, and adjacent thereto, a fourth non-elasticizing peripheral section are provided in the flat state before connecting the longitudinal side edge sections at the manufacturing plant, extending from a longitudinal side edge of the front part or rear part of the article along the periphery of a respective leg opening towards a center crotch line.

In accordance with the invention, it is not necessary to elasticise the entire leg opening of a pants-type diaper. In view of the fact that modern hygiene articles have additional upright collar elements, so-called "cuff elements", which extend substantially in the longitudinal direction and which form a lateral barrier for escaping liquid and solid body excretions, leg openings which are continuously elasticized in the peripheral direction no longer appear to be absolutely necessary. Since the elasticizing means gather or frill the material to which they are connected in the pretensioned state, they accumulate material in the relaxed state which may be uncomfortable e.g. during sitting. In any event, gathered or frilled areas, i.e. elasticized areas, severely rub the skin surface of the user, in particular while he/she is moving, which can cause the above-mentioned skin irritation. It has turned out in accordance with the invention that this can be counteracted by only using elasticizing means in the crotch area at locations where they are actually required. In accordance with the invention, the wearing comfort is improved in that a second non-elasticized peripheral section is disposed between the first peripheral section facing the hip area and the third peripheral section disposed between the legs of the user, and a further non-elasticized fourth peripheral section is provided in the area of a center crotch line. The respective material sections of the second and fourth peripheral section of the hygiene article abut the skin surface of the user with slight pretension. Since the second peripheral section is not subjected to permanently changing gathering or frilling, it does not rub on the surface of the skin. Moreover, air exchange with the inside of the hygiene article is possible, which considerably improves the microclimate in the areas of the skin surface covered by the hygiene article.

An improvement in accordance with the invention is already achieved by providing such a non-elasticized second peripheral section only along the peripheral area of the two leg openings facing the front part. In a further development of this basic inventive idea, the peripheral areas in the front part and also in the rear part are advantageously designed in accordance with the invention such that at least three non-elasticized peripheral sections are provided for each leg opening.

In another advantageous fashion, elasticizing means extending substantially in one transverse direction are provided in the crotch area of the hygiene article. Such an elasticizing means in the area of the absorption body can produce a desired contracting motion of the suction body in the crotch area. The absorption body is advantageously narrow in the crotch area while still providing sufficient absorbing capacity, i.e. absorbent material. The surface density in this area may be increased through contraction in order to provide a large absorption capacity in this area. Moreover, elasticizing means extending in a transverse direction in the crotch area provide the hygiene article with its shape. The crotch area is advantageously cup-shaped.

The elasticising means extending substantially in the transverse direction in the crotch area or the elasticising means may be formed separately from those elasticising means, which elasticize the leg openings. In accordance with a further embodiment of the invention, the elasticizing means of the third peripheral section advantageously merge into the elasticizing means of the crotch area, i.e. form the elasticizing means extending in a transverse direction in the crotch area, in that they merge from their extension in the peripheral direction of the leg openings substantially in the transverse direction. They may thereby branch off in a substantially steady or unsteady curve progression, wherein a steady progression is preferred. The fourth non-elasticized peripheral section may be formed by elasticizing means extending from the third peripheral section along a curve to the left, and then traversing the crotch area in a transverse direction. The fourth, non-elasticized peripheral section advantageously covers the center crotch line.

The center crotch line extends through the minimum width of the crotch area of the hygiene article. When the minimum cannot be uniquely determined, the center crotch line extends through the center of the crotch area of the hygiene article.

The center of the crotch area of a hygiene article can be determined by disposing an elastic thread or rubber band in the shape of a figure eight about the legs of a user standing upright or a user lying prostrate on a flat support, such that the thread or band crosses at one point between the legs. This crossing point is defined as the center of the crotch area of the hygiene article during proper use.

The respective non-elasticized second and/or fourth peripheral sections may just not be provided with elasticizing means. Another feasible and advantageous possibility is that the elasticizing means initially continuously extend in the peripheral direction of the leg openings during production of the inventive hygiene article, and the non-elasticized second and/or fourth peripheral section is/are obtained by cutting through the previously extended elasticizing means. The elasticizing means will then relax or retract unless they are connected, e.g. glued to chassis-forming materials in the second and/or fourth peripheral section. This connection of the elasticizing means should then be limited to the first and third peripheral section which is supposed to be elasticized, so that the cut elasticizing means in the second peripheral section can relax, thereby losing their elasticizing effect on the second peripheral section.

The elasticizing means in the second and/or fourth peripheral section can be separated with one single cut. However, it may be feasible and advantageous to sever the elasticizing means using a plurality of cuts such that the elasticizing means which previously continuously extended in the second and/or fourth peripheral section are divided into a plurality of small sections, in particular, of a length in the millimeter range, thereby losing their elasticizing effect on the second and/or fourth peripheral section. In this case, the elasticizing means may also be connected, e.g. glued, to chassis materials in the second and/or fourth peripheral section without impairing relaxation. The elasticizing means may be easily cut once or several times using laser technology.

In accordance with a further preferred embodiment of the invention, the non-elasticized second and/or fourth peripheral section is obtained in that the previously extending elasticizing means loose their elasticizing effect through application of heat and/or pressure and/or laser. This may be achieved, in particular, through irradiation with ultrasound. It is thereby possible to deactivate a previously extending pretensioned elasticizing means by deforming it, in particular, through punctiform or matrix-like application of pressure and/or temperature, in particular, ultrasound, and, in particular, cutting it such that at least its elasticizing effect on the respective peripheral section is eliminated.

Application of heat and/or pressure is more advantageous than cutting in that it reduces the danger of chassis-forming materials being inadvertently cut or perforated. On the other hand, it may be particularly advantageous to cut or perforate the chassis-forming materials in the area of the second and/or fourth peripheral sections, in order to render the hygiene article more breathable at these locations. In particular, when absorption bodies in the form of a functional unit having an absorbent structure and a liquid-impermeable back sheet are used directly below the absorbent structure, the other chassis materials need not be absolutely impermeable to liquids. It may even be desirable to only use air-permeable chassis materials in order to effect breathability. When the above-mentioned functional units are used as an absorption body, chassis materials of non-woven materials or non-woven laminates may advantageously be used. Non-woven laminates with breathable or even liquid-permeable sheets are also feasible. The above-mentioned functional units used as an absorption body may also comprise integrated top sheet layers, and advantageously upright elasticizing collar elements (so-called "cuffs"), which form a lateral outlet barrier. Such collar elements may also be provided outside of the absorption body or the functional unit used as the absorption body.

In accordance with a further inventive idea, a track is advantageously provided which is continuous in the transverse direction for applying heat and/or pressure and also covers the second and/or fourth peripheral section of the respective leg opening. This track, which continuously extends in the transverse direction, may advantageously be produced through continuous, i.e. non-interrupted processing in the machine direction of the materials forming the hygiene article. This is advantageous with regard to production.

Reference is made to EP 1 374 814 A1, which discloses a technology of applying heat and/or pressure for deactivating elasticizing means, the entire disclosure of which is hereby incorporated by reference.

It has turned out to be suitable and advantageous for the first elasticizing peripheral section to extend in the peripheral direction of the leg openings (best viewed in the "flat state" of the sheet materials forming the hygiene article) by 3 to 15 cm, in particular 4 to 15 cm, in particular 5 to 15 cm, and moreover preferentially 5 to 13 cm. The "flat state" thereby means that the hygiene article is disposed or projected onto a support such that its chassis materials are no longer gathered by the elasticizing means. In correspondence with the above-described position of this first peripheral section, the hygiene article, being readily configured and applied to a user, extends from the side from the apex, facing the hip, of the respective leg opening in the clockwise direction or in an anticlockwise direction.

The second non-elasticized peripheral section advantageously extends in the peripheral direction in the flat state by 1 to 10 cm, in particular 2 to 8 cm and preferentially 3 to 8 cm.

The third, likewise elasticized peripheral section advantageously extends in the peripheral direction in the flat state by 1 to 8 cm, in particular 1 to 7 cm, and preferentially 1 to 5 cm.

The fourth non-elasticized peripheral section advantageously extends in the peripheral direction in the flat state by 1 to 7 cm, in particular 1 to 5 cm, and preferentially 1 to 4 cm.

Further features, details and advantages of the invention can be extracted from the enclosed claims and the drawing and the following description of a preferred embodiment of the inventive hygiene article.

DESCRIPTION OF THE PREFERRED EMBODIMENT

Figure 1:
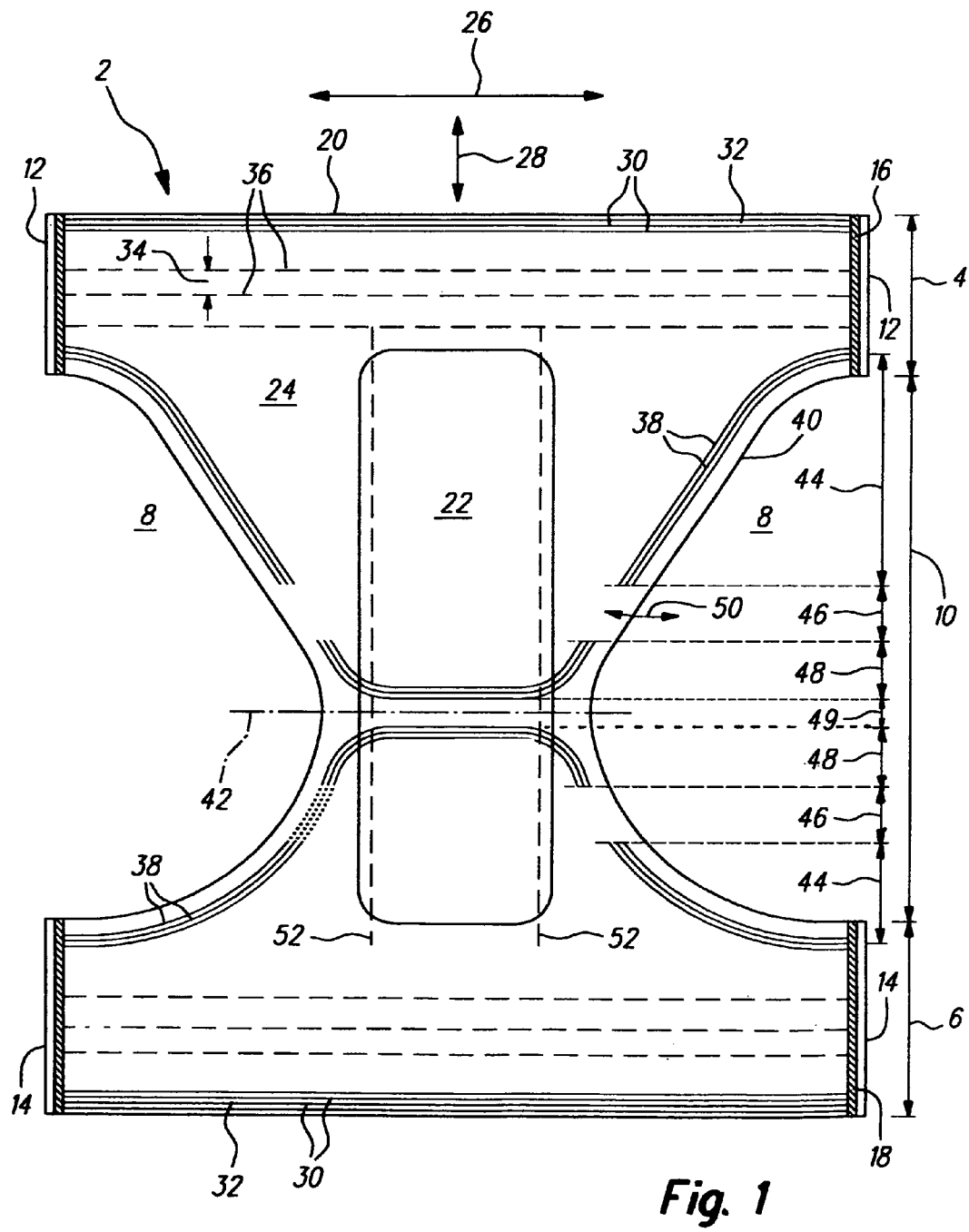
FIG. 1 shows a top view of a first embodiment of an inventive hygiene article in the flat state prior to being connected at the longitudinal side edge areas at the manufacturing plant.

FIG. 1 shows a hygiene article, designated in total with reference numeral 2, in the form of a pants-type diaper ("pants") in the flat state before being connected at the longitudinal side edge sections at the manufacturing plant. The hygiene article comprises a rear part 4, a front part 6, and an intermediate crotch part 10 delimiting the future leg openings 8. In the flat state, the rear part 4 is delimited by longitudinal side edges 12 and the front part 6 is delimited by longitudinal side edges 14. These are connected to each other in the area of the hatched zones 16 and 18 to form the pants shape, i.e.

through hot sealing or other conventional joining methods. In this fashion, two side seam areas of the hygiene article are formed which cannot be released without causing damage. The readily configured hygiene article may have a breaking line, e.g. in the form of a release thread, in particular, along these side seam areas so that the hygiene article can be opened in the applied state. Additionally, any closing elements, i.e. adhesive or mechanically connecting closure shackles may be provided so that the hygiene article can be closed again after opening, like a diaper. The hygiene article is produced by the manufacturer in the form of pants having a hip edge 20, which is closed in the peripheral direction and forms a hip opening, which is limited on all sides. It is therefore a pants and not a diaper, which can be opened and closed.

The hygiene article 2 also comprises an absorbent body 22 which may also be designed as a functional unit, i.e. may have a liquid absorbing structure with a liquid-impermeable back sheet and optionally further components such as e.g. a top sheet and elasticized collar elements, and be disposed as a functional unit onto chassis-forming materials 24 of the hygiene article 2. These chassis-forming materials 24 may e.g. be any back sheet materials or composite materials. Non-woven materials or non-woven laminates and also non-woven sheet laminates are advantageously used which have a textile-like surface and are preferably also breathable, at least in some areas. The chassis-forming materials 24 may also comprise a top sheet layer facing the body, which covers the absorption body 22 and may extend in a transverse direction 26 and/or in a longitudinal direction 28 of the hygiene article 2 up to the edges thereof.

FIG. 1 also shows elasticizing means 30 which continuously extend in the transverse direction 26 and continuously elasticize a hip edge area 32 of the hygiene article 2. Elasticizing means 36 are moreover indicated by dashed lines in the rear part 4 and in the front part 6 at a separation 34 of 5 to 15 mm from each other, which elasticize only regions of the rear part 4 and front part 6 and provide good fit for the hygiene article 2.

Elasticizing means 38 are moreover shown which elasticise sections of the leg openings 8 as described below:

The elasticizing means 38 extend from the longitudinal side edge 12 of the rear part 4 along a periphery 40 of the respective leg opening 8 in the direction towards a center crotch line 42. The elasticizing effect of the elasticizing means 38 is not continuous to the center crotch line 42 but is limited from the longitudinal side edge 12 to a first peripheral section 44 of the leg openings 8. A second non-elasticized peripheral section 46 of the leg openings is adjacent thereto, to which an elasticized third peripheral section 48 is adjacent. This third peripheral section 49 is joined by a fourth non-elasticized peripheral section, which extends over the center crotch line 42. The periphery 40 of the leg openings 8 is therefore not continuously elasticized. It is not elasticized in the rear part 4 and/or front part 6 in respective second peripheral sections 46 and in a fourth peripheral section 49. This means that the chassis materials 24 in these second and fourth peripheral sections 46 and 49 are not disposed against the skin surface of the user by elastically pretensioning the mostly thread-shaped elasticizing means 38, rather softly abut the skin surface. This improves the breathability, i.e. improves ventilation of the areas outside of the absorption body 22, as is indicated by arrow 50. Moreover, the chassis materials 24 are not gathered or frilled in the second and fourth peripheral sections 46 and 49, which increases the skin friendliness, since skin irritation is reduced.

The second peripheral section 46 of FIG. 1 does not have any elasticizing means 38. This may advantageously be achieved in that the elasticizing means 38 initially continuously extend through all three peripheral sections but are connected, preferably glued, to the chassis materials 24 only in the first and third peripheral section 44, 48 in the pretensioned state. The elasticizing means 38 must be merely cut in the second peripheral section 46, and retract due to their pretension, to their fixture in the first and third peripheral sections 44, 48, such that the second peripheral section 46 is no longer elasticized. The fourth peripheral section 49 is thereby not elasticized, such that the elasticizing means 38 extend from their extension in the third peripheral section 46 along a curve to the inside in the transverse direction 26. The fourth peripheral section 49 is thereby formed between the respective third peripheral section 46 of the rear part 4 and the front part 6.

The elasticizing means 38 in the second peripheral section 46 of the front part 6 are shown with dotted lines on the left hand side of FIG. 1. This represents a further embodiment of the invention, in which the elasticizing means 38, which previously continuously extended from the longitudinal side edge 14 to the center crotch line 42, were cut several times in the second peripheral section 46 at a separation of 1 to 3 mm. In this fashion, the elasticizing means 38 in the second peripheral section 46 are deactivated. Cutting the elasticizing means 38 several times can be achieved by a knife roller in a production machine which rolls over the sheet materials transported in the machine direction in the transverse direction 26. In this case, the previously continuously disposed elasticizing means 38 could also be connected, i.e. glued to the chassis materials 24 in the second peripheral section 46, if this seems to be suitable or is desired for production.

In accordance with a further preferred embodiment of the invention which may also be indicated by the dashed lines in the front part 6 in FIG. 1 on the left hand side, the elasticizing means 38 previously continuously extending from a longitudinal side edge to the center crotch line 42 have lost their elasticizing effect in the second peripheral section 46 through application of heat and/or pressure. The elasticizing means 38 may be deactivated or relaxed through application of heat and/or pressure, i.e. through ultrasound welding methods or through a matrix of heating which results in melting. They are thereby substantially destroyed and can no longer elasticise the second peripheral section 46.

Moreover, elasticisation extending in the transverse direction 26 is provided in the area of the center crotch line 42. This is advantageously achieved, as mentioned above, in that the above-mentioned elasticizing means 38 "bend" inwards from their extension in the peripheral direction in the third peripheral section 48, i.e. are deflected in the transverse direction 26, and traverse the crotch area 10 in the transverse direction 26 below the absorption body 22, i.e. between the absorption body 22 and the chassis materials 24, to then further extend steadily and continuously into the periphery of the opposite leg opening 8. This guidance of the elasticizing means 38 starting from the third peripheral section 46 is separately claimed and is regarded as an independent invention, i.e. independently of the further features of the claims. Departing from the above-described methods for relaxing the elasticizing means 28 in the second peripheral section 46, it is possible to continuously guide the elasticizing means 38 in the machine direction, which corresponds, to the transverse direction 26, and to join them to the chassis materials 24 of the hygiene article. This is considered to be particularly advantageous.

Finally, reference is made to the collar elements 52 ("cuffs") provided on both sides of the absorption body 22, which are elasticized and therefore upright, and which form a lateral barrier for leaking body excretions and also retain liquid body excretions in the area above the absorption body 42 until they have been absorbed by the absorption body 22.

Figure 2:
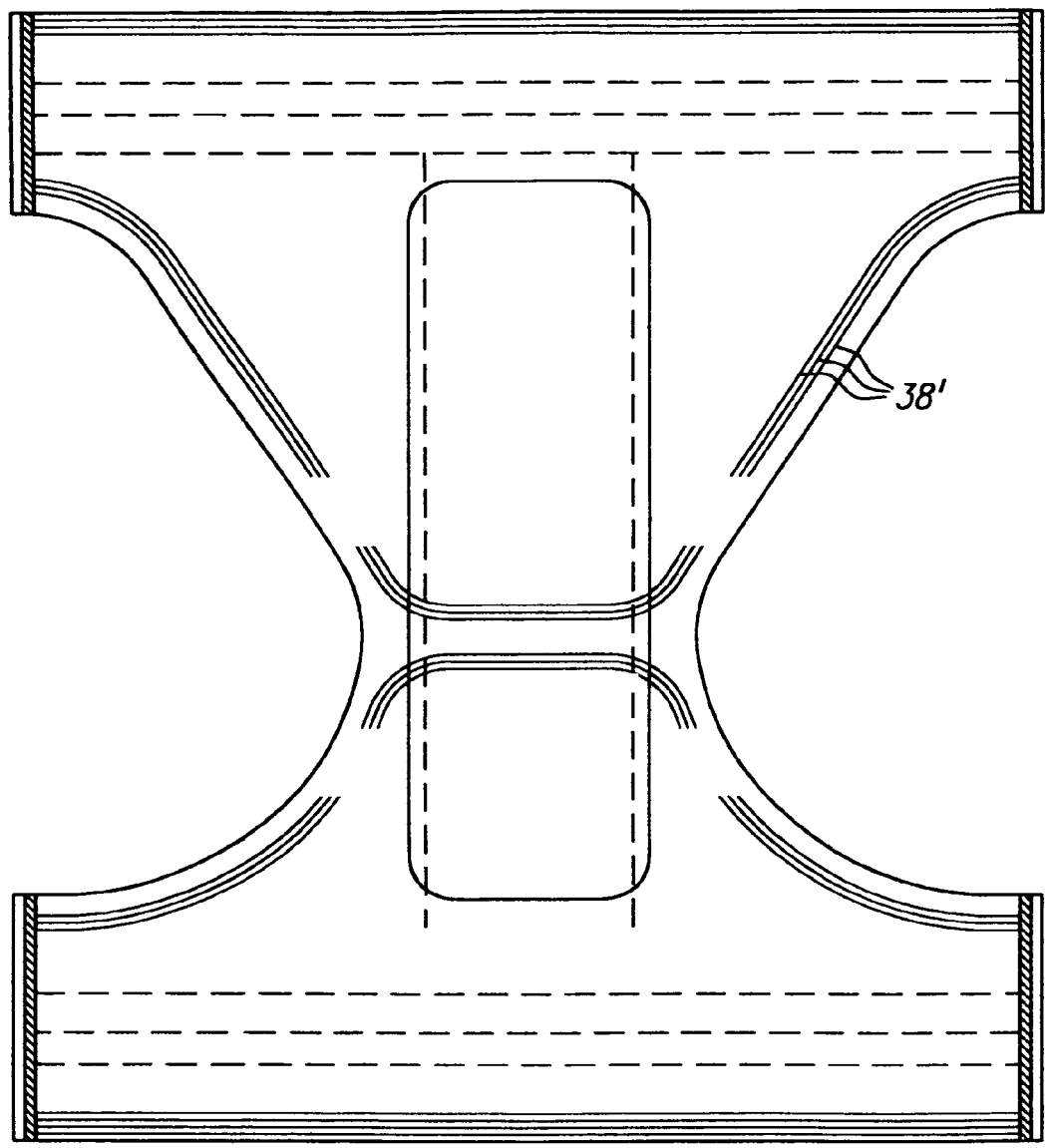
FIG. 2 shows a view of a further embodiment of an inventive hygiene article which corresponds to FIG. 1.

FIG. 2 shows a further embodiment, wherein the elasticizing means 38' traverse the crotch area but are subsequently deactivated in a conventional fashion, i.e. they are cut or rendered non-elasticizing in a different fashion, in particular through application of heat and/or pressure as mentioned above.

We claim:

1. A disposable article, comprising:
    a chassis, having a first waist region, a second waist region, and a crotch region extending in a longitudinal direction of said chassis between said first and said second waist regions, transversely opposite side edges of said first and said second waist regions being bonded together to define a waist opening and two leg openings, wherein a peripheral edge of each of said leg openings comprises a front portion and a rear portion, each of said front and said rear portions of said peripheral edge having a first elasticized section which is located toward a respective front or rear waist region and along which said peripheral edge is elasticized about a respective said leg opening, a second non-elasticized section which is located toward said crotch region and along which said peripheral edge is not elasticized circumferentially about a respective said leg opening, and a third elasticized section which is located, in a longitudinal direction, between said second non-elasticized sections of said front and rear portions of each said leg opening and along which said crotch region is elasticized in a transverse direction of the article;
    a first elastic member extending along said first elasticized section of said front portion of one of said leg openings, across said crotch region in said third elasticized section, and further along said first elasticized section of said front portion of an other leg opening to define a curve convex toward said rear waist regions; and
    a second elastic member extending along said first elasticized section of said rear portion of one of said leg openings, across said crotch region in said third elasticized section, and further along said first elasticized section of said rear portion of an other leg opening to define a curve convex toward said front waist regions.

2. A disposable article, comprising:
    a chassis having a front waist region, a rear waist region, and a crotch region extending in a longitudinal direction of said chassis between said front and rear waist regions;
    transversely opposite side edges of said front and rear waist regions being bonded together to define a waist opening and two leg openings; and
    a peripheral edge of each of the leg openings comprising, in the longitudinal direction, a front portion, a rear portion, and an intermediate portion between the front and rear portions;
    wherein
    each of the front and rear portions of each said peripheral edge comprises
        a first elasticized section which is located toward the respective front or rear waist region and along which the peripheral edge is elasticized about the respective leg opening, and
        a second non-elasticized section which is located toward the crotch region and along which the peripheral edge is not elasticized about the respective leg opening; and
    the intermediate portion defines a third elasticized section which is located, in the longitudinal direction, between the second non-elasticized sections of the front and rear portions of each said leg opening and along which the crotch region is elasticized in a transverse direction perpendicular to the longitudinal direction;
    said article further comprising:
    a first elastic member extending along the first elasticized section of the front portion of one of the leg openings, across the crotch region in the third elasticized section, and further along the first elasticized section of the front portion of the other leg opening to define a curve convex toward the rear waist region; and
    a second elastic member extending along the first elasticized section of the rear portion or one of the leg openings, across the crotch region in the third elasticized section, and further along the first elasticized section of the rear portion of the other leg opening so as to define a curve convex toward the front waist region.

3. The article as set forth by claim 2, wherein
    each of the elastic members is discontinued twice in the respective second non-elasticized sections.

4. The article as set forth by claim 3, wherein
    each of the elastic members in the respective second non-elasticized sections includes several segments severed from each other, whereby elasticity of the severed segments of the elastic member does not affect the inelasticity of the respective second non-elasticized sections.

5. The article as set forth by claim 3, wherein
    each of the elastic members comprises terminal ends in a vicinity of a boundary between (i) the respective first and third elasticized sections and (ii) the respective second non-elasticized sections; and
    said terminal ends of the elastic members are free of direct bonding to said chassis and, hence, do not elasticize the respective second non-elasticized sections.

6. The article as set forth by claim 2, wherein
    each of the elastic members is continuous throughout, but having no elasticity in, the respective second non-elasticized sections.

* * * * *